US00PP36788P2

(12) United States Plant Patent
Mathey

(10) Patent No.: US PP36,788 P2
(45) Date of Patent: Jul. 1, 2025

(54) ***HYDRANGEA* PLANT NAMED 'SMNHAGOV'**

(50) Latin Name: *Hydrangea arborescens*
Varietal Denomination: SMNHAGOV

(71) Applicant: North Carolina State University, Raleigh, NC (US)

(72) Inventor: Megan M. Mathey, Holland, MI (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 18/964,952

(22) Filed: Dec. 2, 2024

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

(56) References Cited

U.S. PATENT DOCUMENTS

PP20,571 P2 * 12/2009 Wood ..... Plt./250

* cited by examiner

*Primary Examiner* — Susan McCormick Ewoldt

(57) ABSTRACT

A new and distinct cultivar of *Hydrangea* plant named 'SMNHAGOV' is disclosed, characterized by large, abundant mophead inflorescences. Sepals open pale white-green, then mature to pure white. Stems are strong and thick, supporting large flower panicles. The new variety is a *Hydrangea*, typically produced as an outdoor ornamental plant.

3 Drawing Sheets

Latin name of the genus and species: *Hydrangea arborescens*.

Variety denomination: 'SMNHAGOV'.

BACKGROUND OF THE INVENTION

The new cultivar is a product of a planned breeding program conducted by the inventor, to produce new *Hydrangea arborescens* with heavy flowering, white sepals, compact habits and strong stems. The open pollination resulting in the new cultivar was made in summer of 2018 at a nursery in Grand Haven, Michigan.

The seed parent is the cultivar *Hydrangea arborescens* 'NCHA5', U.S. Plant Pat. No. 30,296. The pollen parent is unknown. The new cultivar was found and selected by the inventor in summer of 2019 at the same nursery in Grand Haven, Michigan. Asexual reproduction of the new cultivar 'SMNHAGOV' was first performed during the summer of 2019 in Grand Haven, Michigan, by softwood cuttings. Through subsequent propagation, multiple additional generations have been reproduced, having shown that the unique features of this cultivar are stable and reproduced true to type.

SUMMARY OF THE INVENTION

The cultivar 'SMNHAGOV' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNHAGOV'. These characteristics in combination distinguish 'SMNHAGOV' as a new and distinct *Hydrangea* cultivar:

1. Flower sepals which open pale white-green and mature to pure white.
2. Large panicle size.
3. Heavily flowering; superior flower coverage.
4. Strong, thick stems which support large flower panicles without "flopping."
5. Dark green foliage; large globose leaves.
6. Compact, upright habit.

PARENT COMPARISON

Plants of 'SMNHAGOV' are similar to plants of the seed parent in most horticultural characteristics, however, plants of 'SMNHAGOV' differ in the following:

1. Plants of the new cultivar are larger at maturity than plants of the seed parent.
2. Flower sepals of the new cultivar open pale white-green and mature to pure white. Flower sepals of the seed parent open very light pink and mature to white.
3. The new cultivar flowers earlier than the seed parent.
4. Growth habit of the new cultivar is weeping/cascading, while the growth habit of the seed parent is upright.

COMMERCIAL COMPARISONS

Plants of 'SMNHAGOV' can be compared to plants of the commercial cultivar *Hydrangea arborescens* 'Abetwo', U.S. Plant Pat. No. 20,571. Plants of 'SMNHAGOV' are similar to plants of 'Abetwo' in most horticultural characteristics, however, plants of 'SMNHAGOV' differ in the following:

1. Panicle diameter of the new cultivar is slightly smaller, but plant exhibits more flower coverage overall are medium sized. Panicle diameter of this comparator is slightly larger, but plant exhibits less flower coverage overall.

2. Stems of the new cultivar are stronger and more rigid than stems of this comparator.

Plants of the new cultivar *Hydrangea* 'SMNHAGOV' can be compared to the commercial cultivar *Hydrangea arborescens* 'BAlful', unpatented. Plants of 'SMNHAGOV' are similar to plants of 'BAlful' in most horticultural characteristics, however, plants of 'SMNHAGOV' differ in the following:

1. Panicles of the new cultivar are larger than panicles of this comparator.
2. Stems of the new cultivar are stronger and more rigid than stems of this comparator.
3. Plants of the new cultivar have superior resistance to the elements, while plants of this comparator have inferior resistance to the elements.

BRIEF DESCRIPTION OF THE PHOTOGRAPHS

The accompanying photograph in FIG. 1 illustrates in full color a top view of a typical plant of 'SMNHAGOV' grown in a field in Grand Haven, Michigan. This plant is approximately 5 years old.

Figure 1:
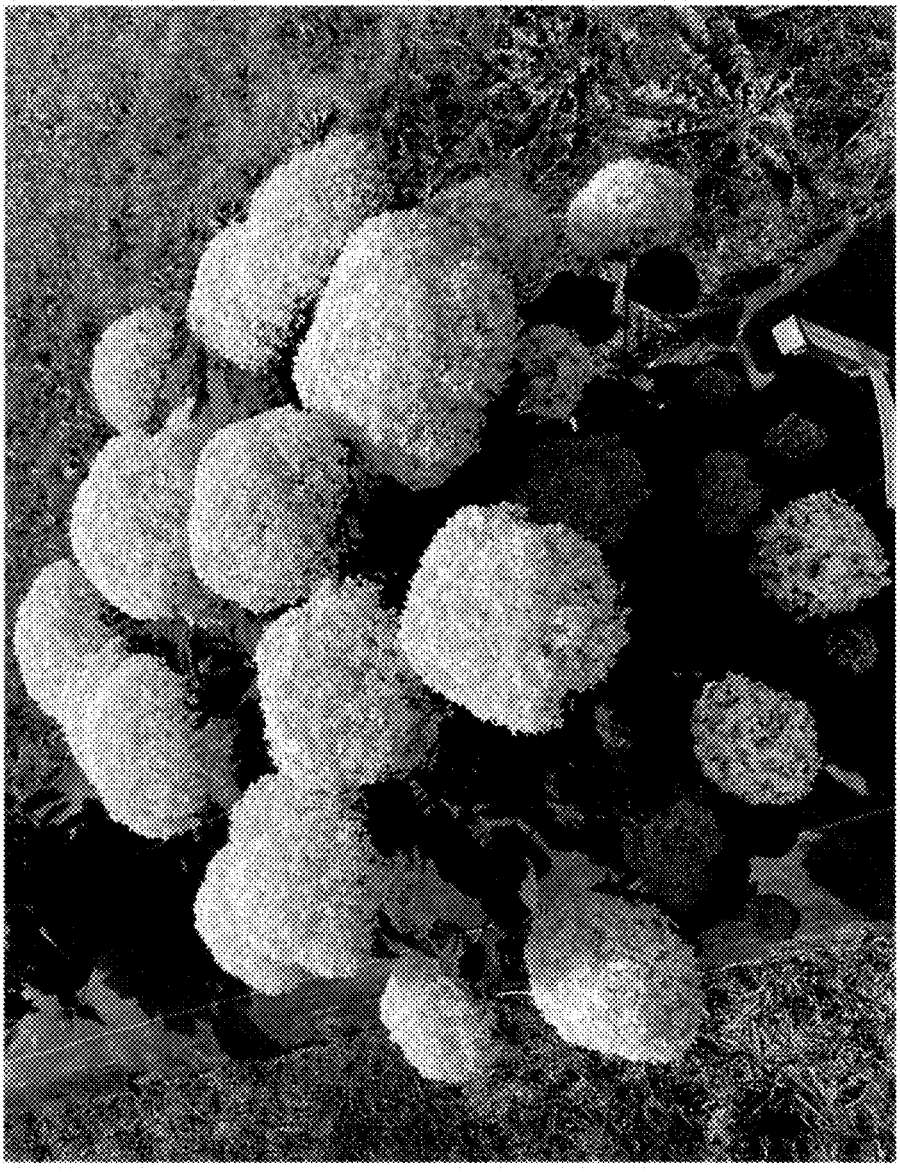
Figure 2:
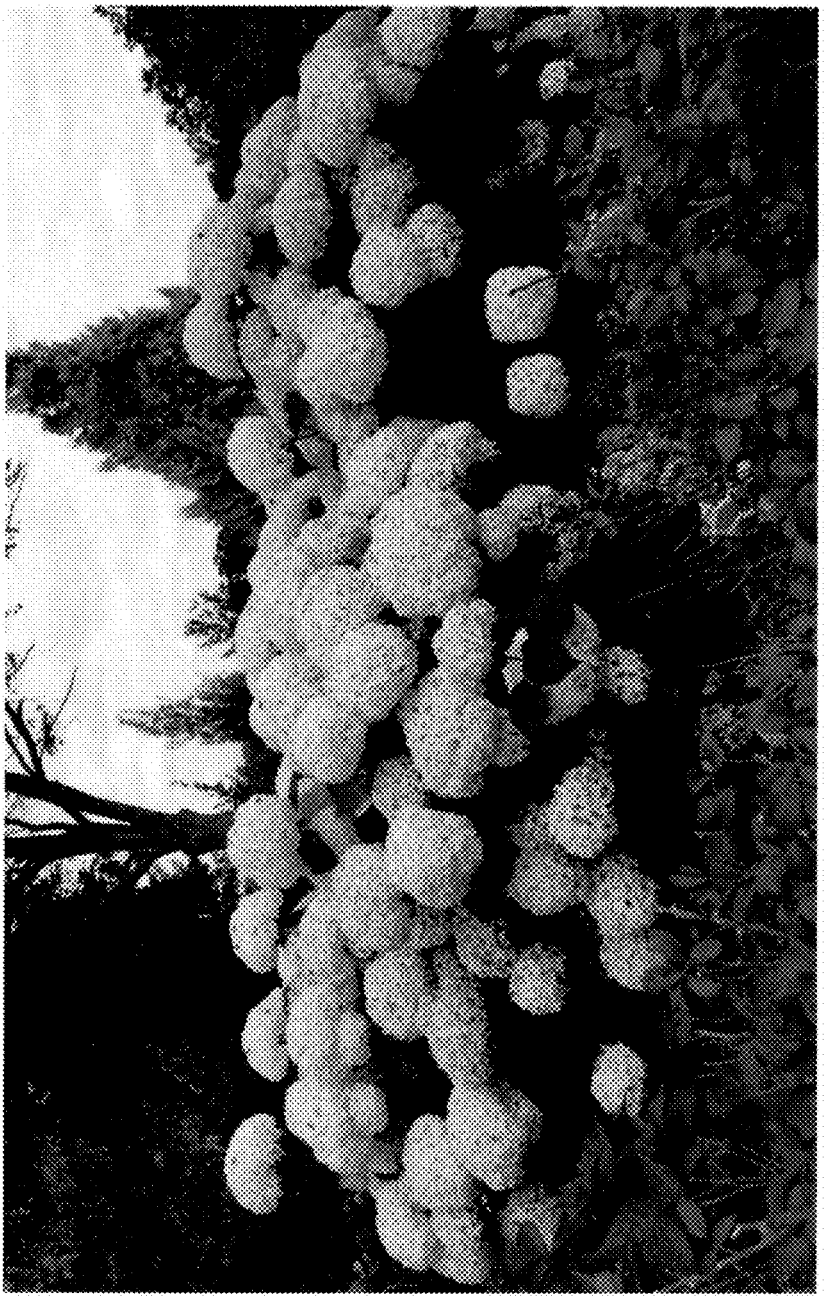
FIG. 2 illustrates in full color a side view of two typical plants of 'SMNHAGOV' grown in a landscape planting in Grand Haven, Michigan. This plant is approximately 5 years old.
Figure 3:
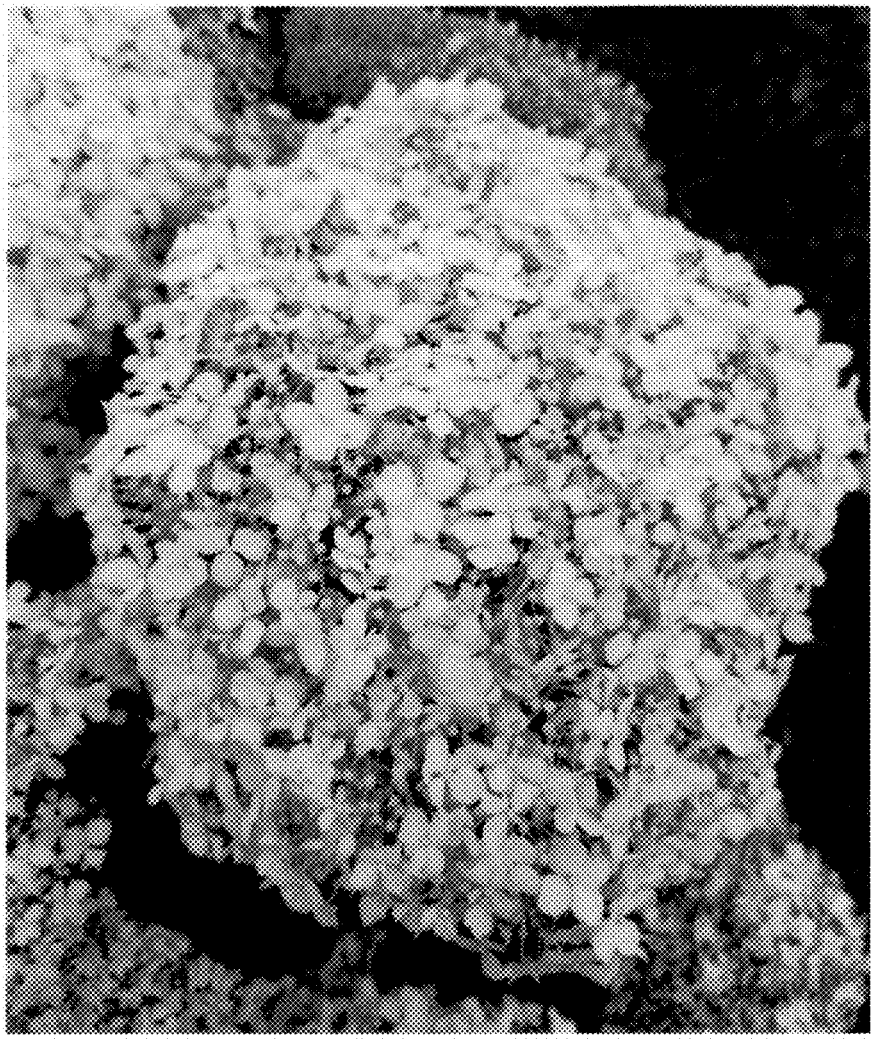
FIG. 3 illustrates in full color a close-up of an inflorescence of 'SMNHAGOV'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'SMNHAGOV' plants grown outdoors in Grand Haven, Michigan. The plants were about 5 years old. Temperatures ranged from 5° C. to 10° C. at night to 18° C. to 27° C. during the day. No artificial light, photoperiodic treatments were given to the plants. Measurements and numerical values represent averages of typical plant types.

Botanical classification: *Hydrangea arborescens* 'SMNHAGOV'.

PROPAGATION

Typical method: Softwood cuttings.

Roots: Thin, freely branching, fibrous, moderately dense. Off-white in color, not accurately measured with R.H.S. chart.

PLANT

Growth habit: Upwards and outwards.
Shape: Compact, rounded.
Height: 100 cm.
Plant spread: 130 cm.
Pot size of plant described: 3-gallon.
Age of plant described: Approximately 5 years.
Growth rate: Moderate to fast.
Plant vigor: High vigor.

Stem:
- *Branching*.—Basal, freely.
- *Number of lateral branches*.—About 40.
- *Shape*.—Rounded.
- *Color*.—Immature: RHS Yellow-Green 144A to 145B. Mature: RHS Grey-Brown 199B.
- *Length*.—85 cm.
- *Width*.—1 cm.
- *Angle*.—60° to 90°.
- *Strength*.—Very strong.
- *Pubescence*.—Slight pubescence on tender growth only.
- *Internode length*.—11 cm on average.

FOLIAGE

Leaf:
- *Arrangement*.—Opposite.
- *Shape*.—Orbicular.
- *Length*.—12 cm.
- *Width*.—11 cm.
- *Apex*.—Caudate.
- *Base*.—Cordate.
- *Margin*.—Serrate.
- *Texture of top surface*.—Very lightly pubescent with a spattering of short, coarse hairs.
- *Texture of bottom surface*.—Slightly pubescent around midrib.
- *Pubescence*.—Yes, both sides.
- *Color*.—Young Foliage, Upper Side: RHS Green NN137B. Young Foliage, Under Side: RHS Yellow-Green 147B. Mature Foliage, Upper Side: RHS Green NN137A. Mature Foliage, Under Side: RHS Green NN137D.

Venation:
- *Type*.—Pinnate.
- *Color*.—Mature, Upper Side: RHS Yellow-Green 146C. Mature, Under Side: RHS Yellow-Green 146C.

Petiole:
- *Length*.—3 cm.
- *Width*.—3 mm.
- *Color*.—Upper Side: RHS Yellow-Green 146C. Under Side: RHS Yellow-Green 146C.
- *Texture*.—Upper Side: Lightly pubescent. Under Side: Lightly pubescent.

INFLORESCENCE

Natural flowering season: June to July.
Inflorescence type: Mophead.
Panicle:
- *Shape*.—Hemispherical.
- *Height*.—15 cm.
- *Diameter*.—20 cm.

Fragrance: None.
Sterile flowers:
- *Flowers per inflorescence*.—2,000 to 3,000.
- *Aspect*.—Upright.
- *Shape*.—Whorl.
- *Length*.—2 cm.
- *Diameter*.—2 cm.
- *Depth*.—3 mm.
- *Persistence*.—Persistent.
- *Longevity*.—Inflorescence remains showy for approximately 4 weeks.

Bud:
*Length.*—2 mm.
*Diameter.*—2 mm.
*Shape.*—Globose.
*Color.*—RHS Green-White 157B.
Petals: Sterile flowers seldom open.
Sepals:
*Number.*—3 to 4.
*Arrangement.*—Whorl.
*Shape.*—Elliptic.
*Tip.*—Mucronate.
*Base.*—Attenuate.
*Margin.*—Entire.
*Length.*—9 mm.
*Width.*—6 mm.
*Texture.*—Upper side: Glabrous; soft and silky. Under side: Glabrous; soft and silky.
*Color.*—When Opening, Upper Side: RHS Yellow-Green 145D. When Opening, Under Side: RHS Yellow-Green 145D. Fully Opened, Upper Side: RHS Green-White 157C. Fully Opened, Under Side: RHS Green-White 157C.
Pedicel:
*Length.*—1 cm.
*Diameter.*—1 mm.
*Angle.*—45° relative to peduncle.
*Strength.*—Good.
*Texture.*—Slightly pubescent.
*Color.*—RHS Yellow-Green 145B.
Fertile flowers:
*Flowers per inflorescence.*—4,000 to 6,000.
*Aspect.*—Upright.
*Shape.*—Whorl.
*Length.*—5 mm.
*Diameter.*—5 mm.
*Depth.*—5 mm.
*Persistence.*—Self-cleaning.
*Longevity.*—1 to 2 weeks on plant.
Bud:
*Length.*—2 mm.
*Diameter.*—2 mm.
*Bud shape.*—Globose.
*Bud color.*—RHS Green-White 157B.
Petals:
*Number per flower.*—5.
*Arrangement.*—Whorl.
*Shape.*—Elliptic.
*Tip.*—Acute.
*Base.*—Blunt.
*Margin.*—Entire.
*Length.*—2 mm.
*Width.*—1 mm.
*Texture.*—Upper Side: Glabrous. Under Side: Glabrous.
*Color.*—When Opening, Upper Side: RHS Yellow-Green 145D. When Opening, Under Side: RHS Yellow-Green 145D. Fully Opened, Upper Side: RHS Green-White 157C. Fully Opened, Under Side: RHS Green-White 157C.
Sepals: Not present.
Pedicel:
*Length.*—5 mm.
*Diameter.*—1 mm.
*Angle.*—45° relative to peduncle.
*Strength.*—Good.
*Texture.*—Slightly pubescent.
*Color.*—RHS Yellow-Green 145B.

REPRODUCTIVE ORGANS

Sterile flower: Sterile flowers seldom open. No reproductive organs have been detected.
Fertile flower:
Stamens:
*Number.*—8 to 10.
*Filament length.*—5 mm.
*Filament color.*—RHS White 155A.
Anthers:
*Shape.*—Globose.
*Length.*—1 mm.
*Color.*—RHS Yellow 4D.
*Pollen amount.*—Sparse.
*Pollen color.*—RHS Yellow 4D.
Pistil:
*Number.*—1.
*Length.*—1 mm.
Stigma:
*Shape.*—Bi-lobed.
*Color.*—RHS White 155A.
*Style length.*—1 mm.
*Style color.*—RHS White 155A.
*Ovary color.*—RHS Yellow-Green 145B.

SEEDS

Quantity: Each flower produces a capsule which gives rise to tens of minute seeds. Seeds are very fine and dust-like.
Shape: Narrowly-elliptic or sickle-shaped.
Length: Less than 1 mm.
Diameter: Less than 1 mm.
Color: RHS Grey-Brown N199B.

OTHER CHARACTERISTICS

Fruit: Not observed.
Disease resistance: Neither resistance nor susceptibility to the normal diseases and pests of *Hydrangea* has been observed.
Drought tolerance and cold tolerance: Hardy to USDA Zones 3-8.
Wind and rain tolerance: Tolerant to wind. Extremely tolerant to rain, possessing strong stems which resist "flopping" even in downpour.

What is claimed is:
1. A new and distinct cultivar of *Hydrangea* plant named 'SMNHAGOV' as herein illustrated and described.

* * * * *